United States Patent
Biedermann et al.

[11] Patent Number: 5,911,697
[45] Date of Patent: Jun. 15, 1999

[54] SPINAL COLUMN ORTHESIS

[75] Inventors: Lutz Biedermann, VS-Villingen; Jürgen Harms, Waldbronn, both of Germany

[73] Assignee: Biedermann Motech GmbH, VS-Schwenningen, Germany

[21] Appl. No.: 08/993,813

[22] Filed: Dec. 18, 1997

[30] Foreign Application Priority Data

Dec. 23, 1996 [DE] Germany ............ 196 54 256

[51] Int. Cl.⁶ .................................................. A61F 5/00
[52] U.S. Cl. ........................................................ 602/19
[58] Field of Search .................... 602/5, 13, 16, 602/19, 20, 23, 24; 128/96.1, 99.1

[56] References Cited

U.S. PATENT DOCUMENTS

| | | | |
|---|---|---|---|
| 2,453,370 | 11/1948 | Hittenberger | 602/19 |
| 4,245,827 | 1/1981 | Mignard | 602/19 |
| 4,285,338 | 8/1981 | Oebster et al. | 602/19 |
| 4,559,933 | 12/1985 | Betard et al. | 602/19 |
| 4,708,130 | 11/1987 | Grudem . | |
| 4,807,605 | 2/1989 | Mattingly | 602/19 |
| 4,905,678 | 3/1990 | Cumins et al. | 602/24 |
| 5,259,831 | 11/1993 | LeBron | 602/7 |
| 5,433,697 | 7/1995 | Cox | 602/19 |
| 5,538,499 | 7/1996 | Schwenn et al. | 602/20 |
| 5,620,412 | 4/1997 | Modglin | 602/24 |

FOREIGN PATENT DOCUMENTS

| | | |
|---|---|---|
| 0 362 049 | 4/1990 | European Pat. Off. . |
| 2 659 547 | 9/1991 | France . |
| 2 696 639 | 4/1994 | France . |
| 30 49 097 | 7/1982 | Germany . |

*Primary Examiner*—Linda C.M. Dvorak
*Attorney, Agent, or Firm*—George W. Neuner

[57] ABSTRACT

A spinal column orthesis system is created which reduces the requirements for stock-keeping various sizes of spinal column ortheses and which enables a better adaptation to the body. The inventive spinal column orthesis comprises a rear member 1 of predetermined height and width, a front member 2 and two side members 3, 4 each connecting the rear member with the front member.

5 Claims, 2 Drawing Sheets

SPINAL COLUMN ORTHESIS

BACKGROUND OF THE INVENTION

The invention relates to a spinal column orthesis.

It is known to form a spinal column orthesis in a single piece. It is therefore necessary to keep a large number of types thereof on stock and to select from stock the particular type which fits the anatomic properties of the individual.

OBJECTS OF THE INVENTION

It is the object of the invention to provide an improved spinal column orthesis in which the above-mentioned drawback is avoided. It is a further object to provide a spinal column orthesis which facilitates the stock-keeping of spinal column ortheses and allows a better adaptation to the physical characteristics of the individual.

SUMMARY OF THE INVENTION

In order to achieve the above-mentioned objects the invention provides a spinal column orthesis comprising a rear member having a predetermined height and width, a front member and two side members each connecting the rear member with the front member and embracing the pelvis.

BRIEF DESCRIPTION OF THE DRAWINGS

Further features and advantages of the invention will be apparent from the description of an embodiment with reference to the Figures. In the Figures.

DESCRIPTION OF A PREFERRED EMBODIMENT

Figure 1:
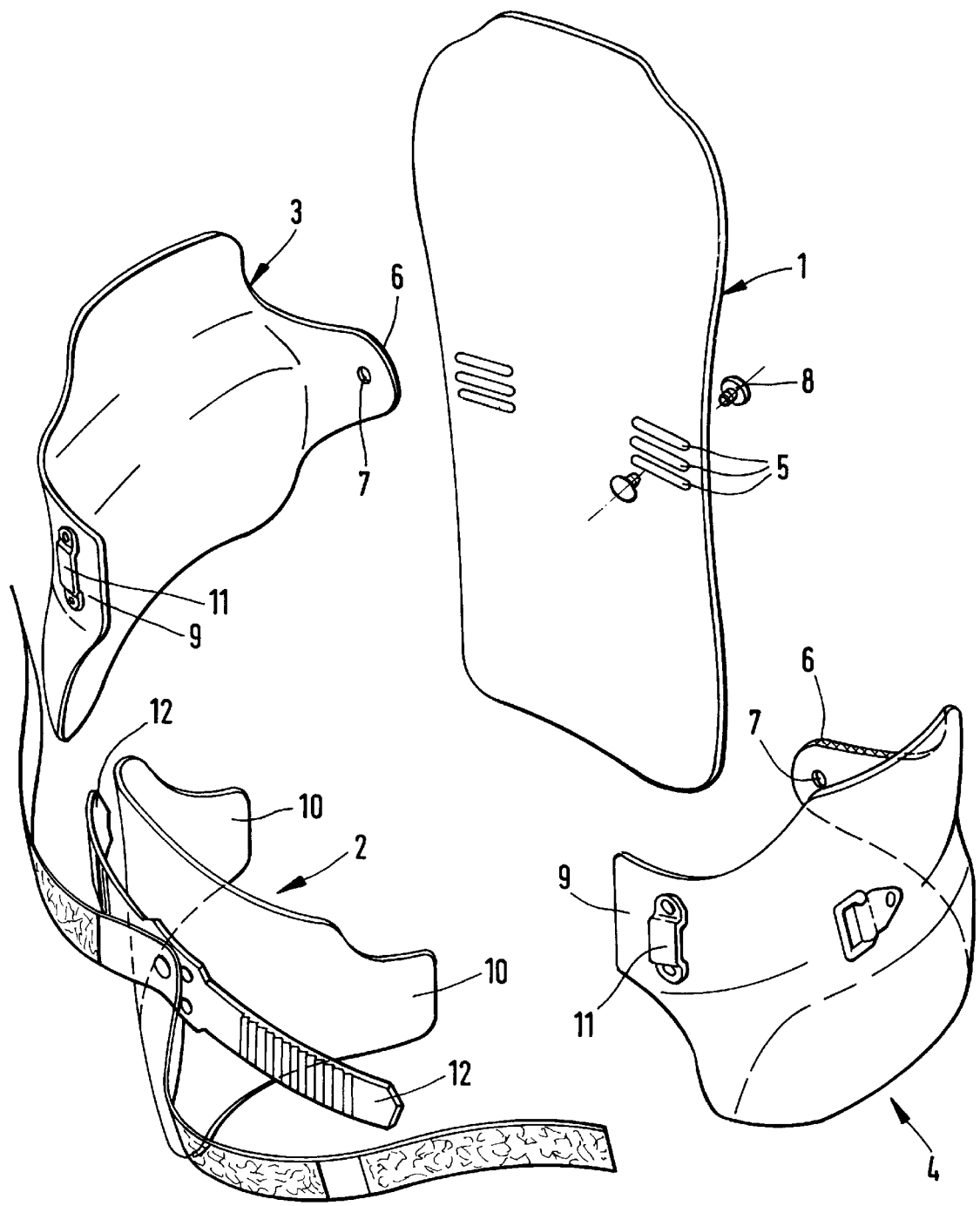
FIG. 1 shows the members of the spinal column orthesis without internal padding in an exploded representation and FIG. 2 is a perspective view of the assembled spinal column orthesis.

The spinal column orthesis comprises a rear member 1, a front member 2, a first side member 3 and a second side member 4. Each member has an outer hard shell which is shown in FIG. 1 and an inner padding referred to in FIG. 2 by the reference signs 1', 2', 3' and 4'.

The shape of the rear member 1 comprising the hard shell and the padding 1' is adapted to the usual rear part of a spinal column orthesis. Elongate holes 5 extending in latitudinal direction are arranged on both sides in the region of the rear member where the side members 3, 4 are to be mounted to the rear member. A central elongate hole extends in latitudinal direction at a height which corresponds to a normal elevation of the joint between the side members and the rear member. Corresponding further elongate holes are arranged parallel to the central elongate hole at a small distance thereabove and therebelow.

The shape of the hard shell of one side member 3 and of its associated padding 3' is a mirror image of that of the other side member 4 and its padding 4'. Each member is adapted to the hip regions in the same manner as the side part of the known single-piece spinal column orthesis. The side members have hinge portions 6 for connection to the rear member, which hinge portions comprise a connection hole 7 receiving a connecting bolt 8. The adjustment of the connection in longitudinal and latitudinal direction is made by selecting one of the elongate holes and of the position of the connecting bolt within the selected elongate hole, followed by tightening the connecting bolt 8. The side of the side members 3, 4 opposite to the hinge portion 6 comprises a connecting portion 9 for connection with the front member 2.

The hard shell of the front member 2 shown in FIG. 1 and the associated padding 2' are preformed to fit the abdominal region in the same manner as the abdominal portion of a one-piece spinal column orthesis. The front member has a central portion and two lateral connecting wings 10 for connection with the side members.

The central portion comprises a belt band 12 having its central part mounted to the front member and a respective free end on both sides thereof. Buckles 11 engaging the free ends of the belt band 12 are provided at the connecting portions 9 of the side members 3, 4.

Figure 2:
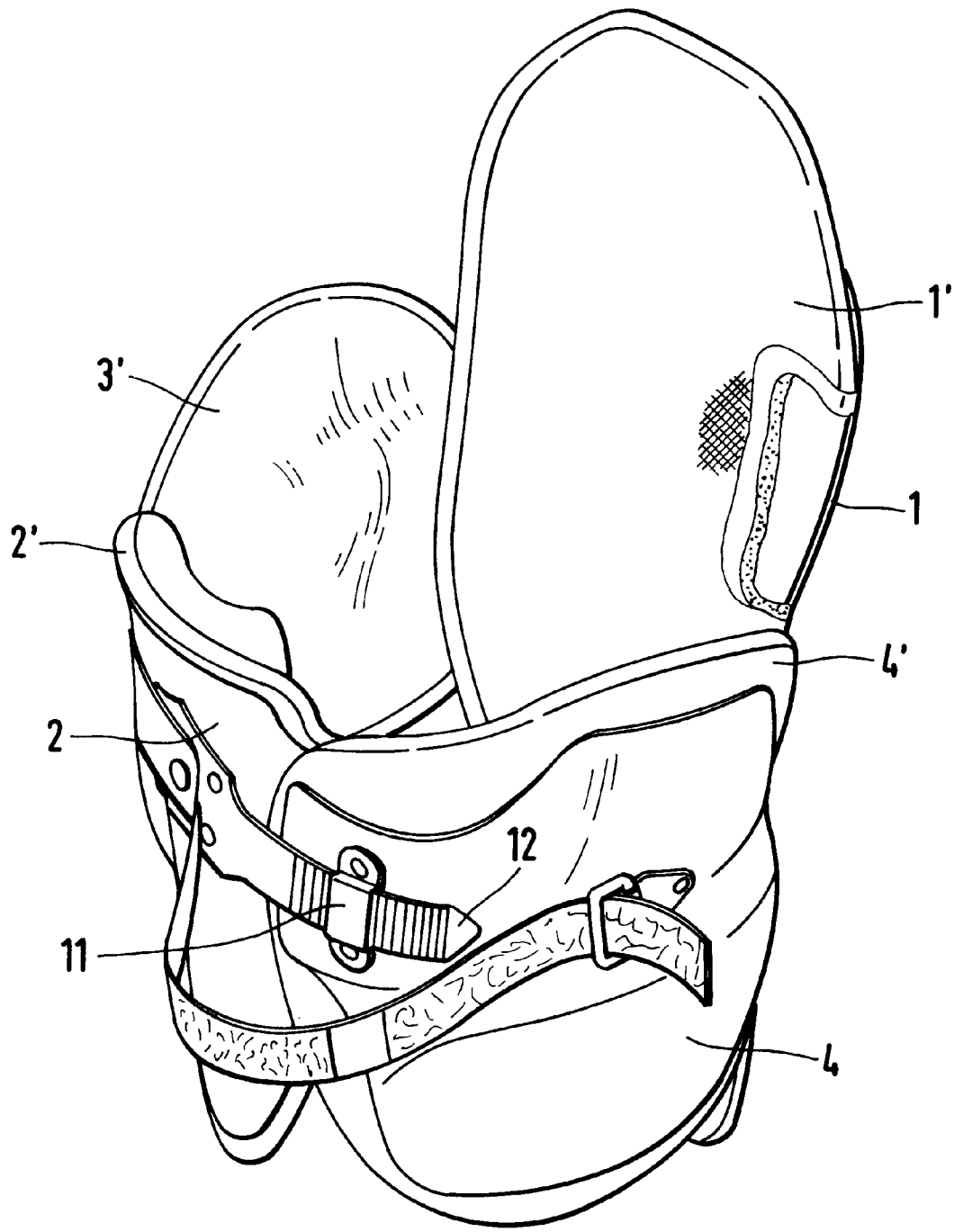

For assembling the orthesis in the manner shown in FIG. 2 the free end of the side members having the hinge portion 6 engages the back side of the rear member 1 and the corresponding free end forming the connecting portions 9 engages the outer side of the connecting wing 10 of the front member 2. After having selected the longitudinal and lateral position of the side members by selecting the position in the elongate holes 5 the size of the central portion is adapted by selecting the corresponding degree of superposition of the two side members over the central portion or front member and using the belt band 12 for fixing this relative position.

Although the invention has been described with reference to a specific example embodiment, it is to be understood that it is intended to cover all modifications and equivalents within the spirit and scope of the appended claims.

We claim:

1. A spinal column orthesis comprising:

two side members, each being formed to embrace the pelvis, a rear member having a predetermined height and width, and a front member having a central portion and connecting wings on each side, wherein the side members, the rear member and the front member each include a preformed outer hard shell, wherein the rear member is hinged to each of the side members, and wherein the side members and the central portion include an adjustable connection.

2. The spinal column orthesis of claim 1, comprising means for connecting said rear member to a respective one of said side members at selective positions in longitudinal and latitudinal direction of said rear member.

3. The spinal column orthesis of claim 2, wherein said connecting means comprises at least one elongate hole adapted to receive a connecting member, said elongate hole being formed in said rear member or in said side member and extending in longitudinal or latitudinal direction.

4. The spinal column orthesis of claim 1, wherein said side members have connecting portions for connection to said rear member and to said front member, said connecting portions engaging the outer surface of said rear member and of said front member.

5. The spinal column orthesis of claim 1, wherein said adjustable connection comprises a belt band and buckles.

* * * * *